(12) United States Patent
Pickert et al.

(10) Patent No.: US 6,732,572 B1
(45) Date of Patent: May 11, 2004

(54) METHOD AND DEVICE FOR MONITORING AND/OR DETERMINING MOTOR OIL QUALITY

(75) Inventors: Detlef Pickert, Wolfsburg (DE); Volker Schumacher, Sassenburg (DE); Harald Sölter, Braunschweig (DE); Martin Völtz, Norderstedt (DE)

(73) Assignee: Volkswagen AG, Wolfsburg (DE)

( * ) Notice: Subject to any disclaimer, the term of this patent is extended or adjusted under 35 U.S.C. 154(b) by 0 days.

(21) Appl. No.: 09/530,936

(22) PCT Filed: Nov. 4, 1998

(86) PCT No.: PCT/EP98/06966

§ 371 (c)(1),
(2), (4) Date: Aug. 18, 2000

(87) PCT Pub. No.: WO99/24699

PCT Pub. Date: May 20, 1999

(30) Foreign Application Priority Data

Nov. 7, 1997 (DE) .......................................... 197 49 364

(51) Int. Cl.[7] .............................................. G01N 33/30
(52) U.S. Cl. ..................................... 73/54.01; 73/53.05
(58) Field of Search ............................. 73/53.01, 53.05, 73/53.06, 54.01, 54.02, 54.23, 54.28, 54.29, 54.31, 54.32

(56) References Cited

U.S. PATENT DOCUMENTS

| 4,677,847 A | | 7/1987 | Sawatari et al. | |
|---|---|---|---|---|
| 4,706,193 A | * | 11/1987 | Imajo et al. | 73/117.3 |
| 4,796,204 A | * | 1/1989 | Inoue | 73/117.3 |
| 4,847,768 A | * | 7/1989 | Schwartz et al. | 73/117.3 |
| 4,888,976 A | * | 12/1989 | Vermeiren | 73/10 |
| 5,060,156 A | | 10/1991 | Vajgart et al. | |
| 5,377,531 A | * | 1/1995 | Gomm | 340/457.4 |
| 5,604,441 A | | 2/1997 | Freese, V et al. | |
| 5,750,887 A | * | 5/1998 | Schricker | 73/117.3 |
| 5,969,601 A | * | 10/1999 | Sato et al. | |
| 6,037,864 A | * | 3/2000 | Sem et al. | |
| 6,208,245 B1 | * | 3/2001 | Post et al. | |
| 6,216,528 B1 | * | 4/2001 | Carrell et al. | 73/54.01 |
| 6,223,589 B1 | * | 5/2001 | Dickert et al. | 310/311 |
| 6,253,601 B1 | * | 7/2001 | Wang et al. | 73/117.3 |

FOREIGN PATENT DOCUMENTS

| DE | 32 28 195 | 2/1983 | |
|---|---|---|---|
| DE | 41 31 969 | 4/1993 | |
| EP | 0 174 601 A1 | 3/1986 | |
| EP | 0 174 601 B1 | 1/1990 | ........... F01M/11/10 |

* cited by examiner

Primary Examiner—Eric S. McCall
(74) Attorney, Agent, or Firm—Kenyon & Kenyon

(57) ABSTRACT

The present invention provides a method and device for determining the viscosity of motor oil in an internal combustion engine comprising: measuring frictional torque of the engine based on engine data, such as, the clutch switch signal which shows whether the clutch is engaged transmitting torque to the drive train; a generator load signal, a starter load signal, acceleration power consumption, and the like.

9 Claims, 2 Drawing Sheets

METHOD AND DEVICE FOR MONITORING AND/OR DETERMINING MOTOR OIL QUALITY

FIELD OF THE INVENTION

The invention relates to a method and device for monitoring and/or determining motor oil quality by determining the viscosity of the motor oil being used by internal combustion engines.

BACKGROUND OF THE INVENTION

Many known devices such as machine tools and motor vehicles must be serviced in certain intervals in order to ensure their reliability and extend their service life. The motor oil used by the engine of a motor vehicle is subject to degradation and must be changed after reaching a certain degree of degradation, to avoid engine damage due to insufficient lubrication and cooling. The service life of a motor oil depends, however, on many operating parameters, such as environmental conditions and the driver's driving style. Since these are not predictable, certain safety margins are used and the manufacturer specifies fixed service intervals and oil change intervals for the sake of simplicity, expressed, for example, as fixed mileage figures, and which must be observed for the manufacturer's warranty to remain valid. This results in the vehicle owner often having the vehicle serviced or the oil changed without any valid technical reason, which represents a considerable additional cost factor. Therefore, considerable efforts have been made for some time to match the oil change intervals to the actual degradation of the motor oil.

Known methods for directly determining the degree of motor oil degradation or contamination include, for example, measuring the electrical resistance of the oil the pressure differential between upstream and downstream sides of the oil filter, transparency, or chemical composition of the motor oil. The disadvantage of these direct methods is the additional cost of measuring, for example, the need for additional and special sensors, etc. Therefore, in addition to direct measuring methods, there are methods in which the degree of degradation of the motor oil is determined from operating parameters of the engine or the vehicle that are known otherwise.

European Patent 174 601 discloses a warning system that measures and displays the degradation or aging of the oil in an internal combustion engine and emits a warning signal. The condition of the oil is evaluated and the result of the evaluation is output based on engine parameters such as rotation speed, instantaneous engine load, and oil temperature.

German Patent 41 31 969 presents a lubricating oil monitoring system, in which the oil parameters such as pressure, temperature, and viscosity are measured using a special sensor chip and the actual condition of the motor oil is derived from these parameters. The viscosity of the motor oil is determined using capacitive measurement of the dielectric constant of the oil at two different frequencies. As an alternative, the viscosity of the motor oil can also be determined by measuring sound wave dampening in the motor oil.

German Patent 32 28 195 discloses a method and a device for monitoring the time for a lubricating oil change in a vehicle engine. One essential step of this method is the determination of the contaminant level in the motor oil, which can be derived from the operating conditions of the engine, the level of contaminants being in direct relationship to the viscosity of the motor oil.

The disadvantage of the known methods is that either additional sensors are needed or the conclusion regarding the degree of degradation of the motor oil from known operating parameters does not have the required accuracy and therefore, for safety reasons, the motor oil is changed too early, resulting in extra cost to the owner of the vehicle.

OBJECTS AND SUMMARY OF THE INVENTION

An object of the present invention is therefore to develop a method and device that provide for the motor oil quality of a motor vehicle engine to be monitored and/or determined in a simple and accurate manner.

This object is achieved by determining and evaluating changes in oil viscosity as a function of temperature and engine frictional torque. The method according to the present invention allows changes in motor oil viscosity, which in turn are used for monitoring the motor oil quality, to be determined in a reliable manner as a function of the engines temperature and frictional torque. If the motor oil quality is known, an oil change is not required until the motor oil has actually degraded.

In a preferred embodiment of the method the engine frictional torque is derived from the starting torque. This allows the engine frictional torque to be determined in a simple manner.

In another advantageous embodiment of the present invention, the starting torque is determined from the electric power consumed by the starter during start, with the starter characteristics being known. This method is particularly simple, since current consumption essentially corresponds to the battery load and is therefore easy to determine. Current consumption as a function of motor oil quality is therefore simple to use for determining or evaluating quality.

Advantageously, changes in viscosity are not taken into account unless the value (actual value) is outside a range of −15% to +50% of a predefined viscosity value at the same temperature. This prevents slight variations in viscosity due to different marginal parameters resulting in an "oil change needed" display. It is ensured that only significant changes are taken into account in monitoring and subsequent action is not taken before the right time.

The object of the present invention is furthermore achieved by determining motor oil quality, particularly the viscosity, in an internal combustion engine as a function of engine temperature and frictional torque. By determining the viscosity of the motor oil from the engine frictional torque, with the latter being determined from data present in an engine controller, the proper time for oil change is determined in a simple manner.

In the case of a gasoline engine, the following engine data may be advantageously used for determining the engine frictional torque; i) injection time and/or throttle valve position to determine the engine torque produced; ii) a clutch switch signal, showing whether torque is being transmitted to the drive train; iii) the load signal of the generator to determine the generator drive torque; iv) and signals concerning the operating state of any other auxiliary devices directly driven by the engine. Thus, reliable determination of the motor oil quality is provided.

In a diesel engine, the following engine data may be for determining the frictional torque; i) a clutch switch signal, which shows whether torque is being transmitted to the drive train; ii) the generator load signal as a measure of the electric power generated by the generator; iii) engine rpm; the injected amount of fuel; the engine temperature; and iv) the ambient temperature. This allows the engine oil quality to be reliably determined.

The object of the present invention can also be realized using a method of determining the motor oil viscosity in an internal combustion engine. By measuring the time from start at the engine to the moment when the starter disengagement speed is reached, so that if the constant fuel amount injected during this time is known, the engine frictional torque can be derived from the measured time, and the motor oil quality can be reliably and accurately estimated therefrom.

The object of the present invention can also be realized using a device for carrying out the method. In order to determine viscosity, this device has a control unit for processing and transforming data and at least one memory, with the characteristic curves, needed for determining the viscosity being stored in the memory or in each memory. Such a device allows the motor oil quality to be determined in a simple manner, since no additional measuring means are needed.

BRIEF DESCRIPTION OF THE DRAWINGS

Preferred embodiments are explained in detail below with reference to the drawings.

DETAILED DESCRIPTION OF THE INVENTION

Figure 1:
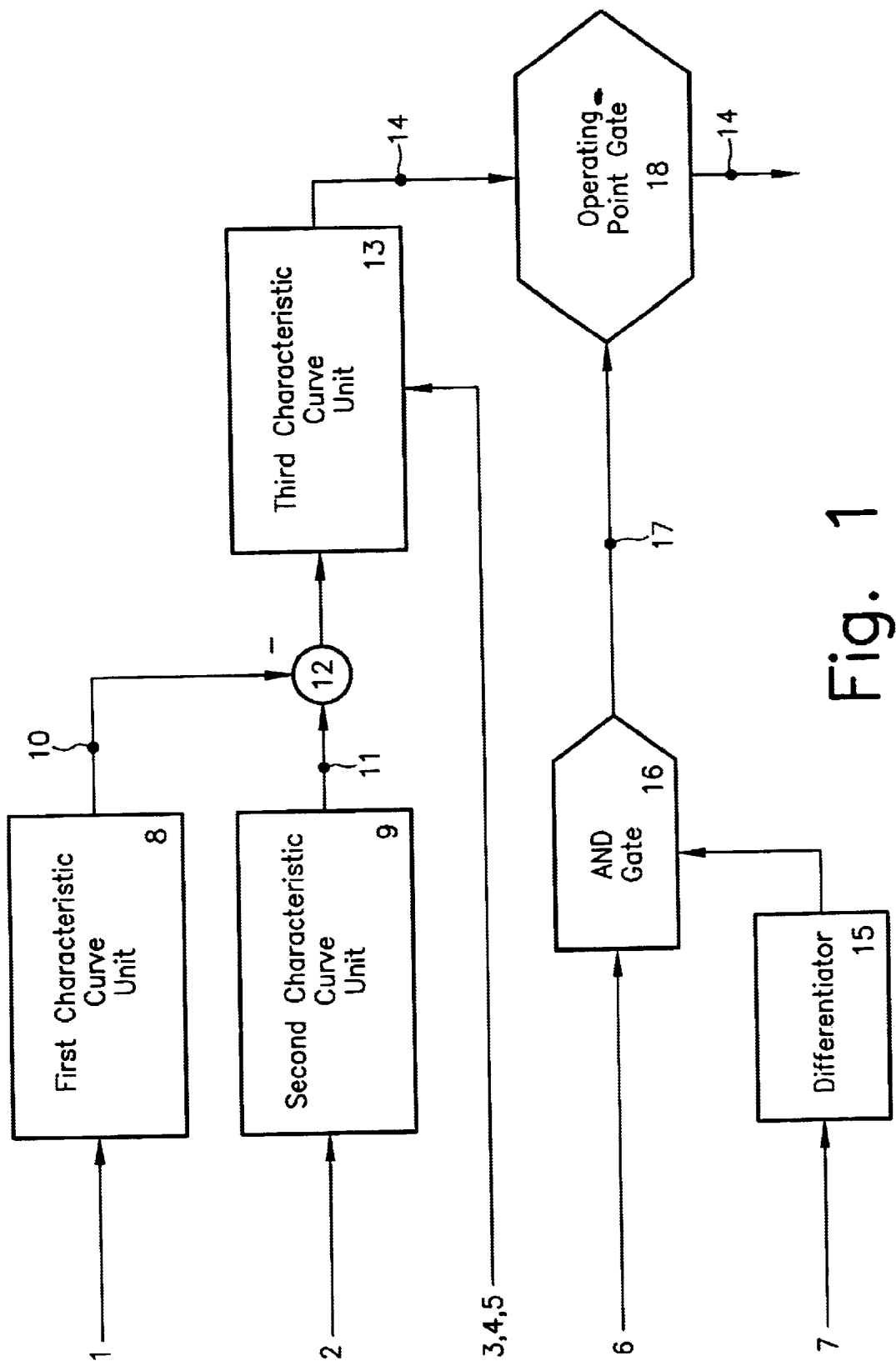
FIG. 1 shows a diagram for determining the oil viscosity in a diesel engine.

The calculation method illustrated in FIG. 1 is based on the torque equilibrium of the engine that is not in gear and is idling. In this mode of operation, most quantities are constant, so that their effect on the engine torque generated can be stored in characteristic maps, preferably in the form of lookup tables.

The stationary torque equilibrium of an engine can be written as $$M_{engine} = M_{clutch} + M_{aux.devices} + M_{friction} + M_{compression} \quad (1)$$

where $$M_{aux.devices} = M_{water\ pump} + M_{oil\ pump} + M_{generator} \quad (2)$$

if no other auxiliary devices are connected.

Under idling conditions, i.e., not in gear, the following equations apply:

$$M_{clutch} = 0 \text{ (any load is disengaged)} \quad (3)$$

$$N_{engine} = \text{constant} \rightarrow dN/dt = 0 \text{ (idling speed is controlled)} \quad (4)$$

$$M_{water\ pump} = \text{constant} \quad (5)$$

$$M_{generator} = f(P_{electric}) \quad (6)$$

(generator torque is a function of electric power)

$$M_{compression} = f(T_{engine}, T_{ambient}) \quad (7)$$

(engine compression torque is a function of engine temperature and ambient temperature)

$$M_{friction} + M_{oil\ pump} = f(V_{oil}, T_{engine}, T_{ambient}), \text{ and} \quad (8)$$

$$M_{engine\ idling} = f(V_{oil}, T_{engine}, T_{ambient}) + M_{generator} = f(m_E) \quad (9)$$

(engine torque when idling is a function of the amount of fuel injected).

Therefrom the viscosity is determined assuming the validity of the above equations (3) to (9) during idling:

$$V_{oil} = f(M_{engine\ idling} - M_{generator}, T_{engine}) \quad (10)$$

At a reference temperature $T_0$ of the oil, which may be 40° C. or 100° C., for example, we obtain:

$$V_{oilT0} = f(V_{oil}, T_{oil}/T_0) \quad (11)$$

The following definitions apply:

M=torque; N=rpm; T=temperature; P=power, $M_E$=injected amount; v=viscosity.

The indices used are self-explanatory.

FIG. 1 shows the diagram for this calculation using the example of a diesel engine. Generator signal 1, which is a measure of the electric power $P_{electric}$ generated by the generator, the injected amount $m_E$ 2, engine temperature $T_{engine}$ 3, ambient temperature $T_{ambient}$ 4, and oil temperature $T_{oil}$ 5, as well as clutch signal 6, which shows whether or not the clutch is engaged, and engine rpm N 7 are available. Generator signal 1 is recalculated into the respective generator torque 10 via a first characteristic map stored in first characteristic map unit 8. In the same manner, injected amount 2 is recalculated into the engine idling torque $M_{engine\ idling}$ 11 via a second characteristic map stored in a second characteristic map unit 9. Forming the difference between the two torques 10 and 11 thus obtained in subtractor 12, the desired frictional torque of equation (9) is obtained, which is a function of oil viscosity. Oil viscosity 14 at the reference temperature is calculated according to equations (10) and (11) via a third characteristic map stored in a third characteristic map unit 13, taking into account engine temperature 3, ambient temperature 4, and oil temperature 5. Characteristic curves or characteristic maps stored in characteristic curve units 8, 9, and 13 are engine-specific and are determined empirically. Since the engine rpm is kept constant by the idling controller, it does not have to be taken into consideration in the non-linear characteristic curve functions in characteristic map units 8, 9, 13. The time derivative of engine rpm 7 is calculated in differentiator 15. The engine rpm differential is ANDed with clutch signal 6 in AND gate 16 to form operating point signal 17. In another logic gate or operating point gate 18, operating point signal 17 of AND gate 16 determines whether or not the determined normalized oil viscosity 14 is valid, i.e., whether the boundary conditions (3) and (4) of equations (10) and (11) are met.

Figure 2:
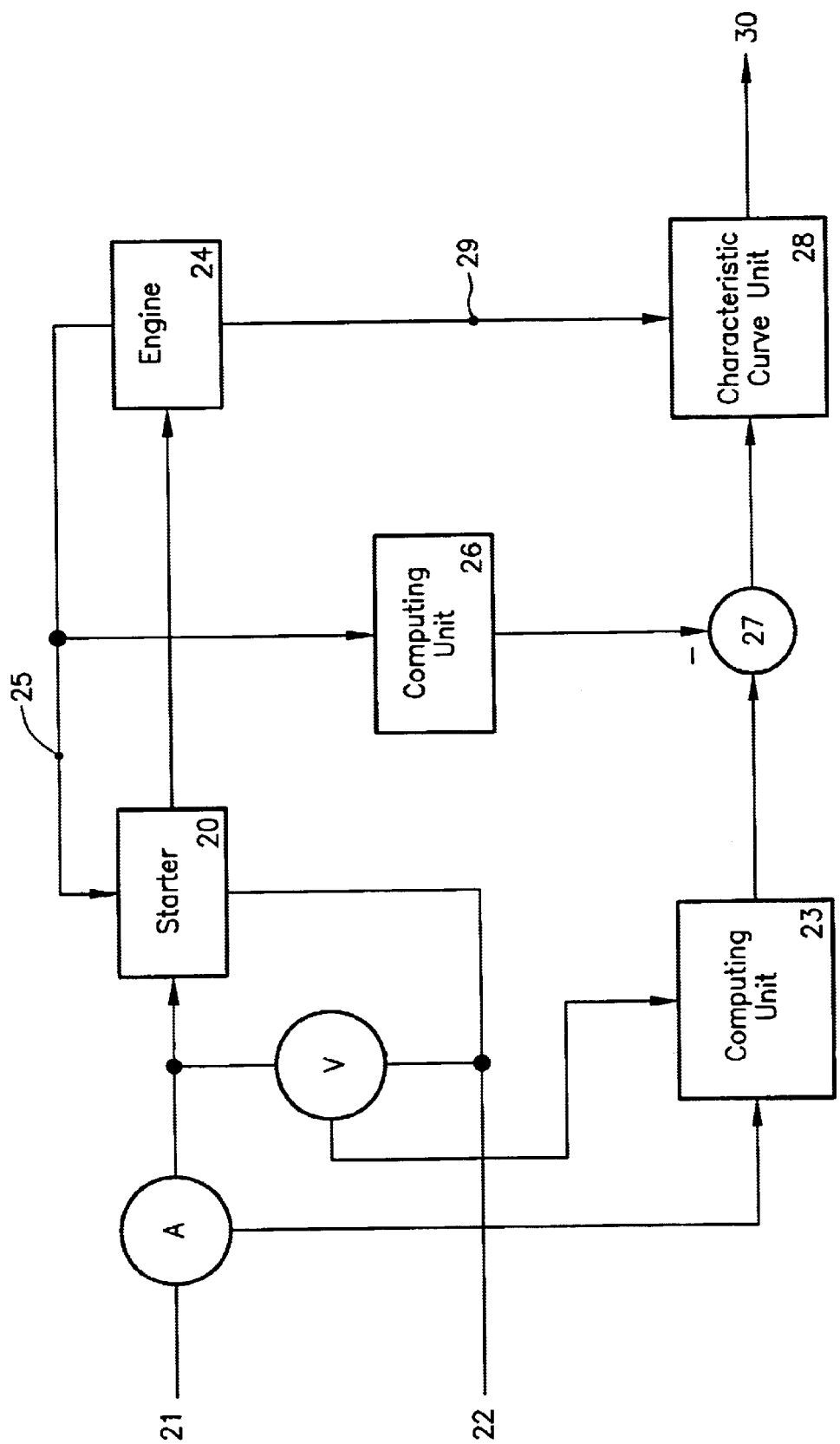
FIG. 2 shows a diagram for determining the viscosity from the electric power consumption of a starter.

The method illustrated in FIG. 2 for determining oil viscosity is based on the evaluation of the energy equilibrium of the, start sequence. Since all loads are basically turned off here and the generator delivers almost no electric power in this rpm range, the generator torque can be assumed, in a first approximation, to be the same for each start, as can the load torques caused by the other auxiliary devices (with the exception of the oil pump), assuming the same ambient conditions. The engine frictional torque and the compression energy can also be assumed to be functions of the engine temperature and time. Since the engine frictional torque and, in particular, the drive torque of the oil pump furthermore depends basically on the motor oil viscosity, the latter can be determined from the differences between the starter power and the known reference conditions during a start sequence.

FIG. 2 shows a starter 20, which is powered via leads 21 and 22 during start. The respective current and voltage are determined by appropriate instruments A and V. A computing unit 23 calculates the starter power according to $$P_{starter} = \eta_{starter} * I * U \quad (12)$$

The starter torque generated by starter 20 is applied to an engine 24. The acceleration power of engine 24 is determined by another computing unit 26 from the engine rpm 25 generated according to $$P_{accel.} = N * \Theta * dN/dt \quad (13)$$

Difference ΔP between starter power and acceleration power, determined in subtractor 27, is the desired friction power of the engine, which corresponds to a frictional torque. Oil viscosity 30 is determined from the frictional torque in a characteristic map unit 28, taking into account engine temperature 29 using the equation $$V_{oil} = f(\Delta P, T_{engine}). \quad (14)$$

The notations used are defined as follows:
P=power, η=efficiency; I=current; U=voltage;
N=rpm; Θ=moment of inertia; ΔP=friction power.

In a third embodiment (not illustrated), the time from start to the moment when the starter disengagement rpm is reached is measured during the start sequence. An engine controller injects a fixed amount of fuel during start, until the starter disengagement rpm is reached. Then the controller switches over to regular idling control. The exact moment of switch-over depends on the torque equilibrium of the engine in the start phase. Since the variation in the torque generated results from the injected fuel amount and is known, the torque loss, i.e., the engine frictional torque, can be estimated from the time elapsed until the starter disengagement speed is reached. The viscosity of the motor oil can thus be estimated from the additional load using reference tests. The "engine regular mode status bit" signal from the engine controller can be used for this measurement. This bit is "0" in the start phase and is set to "1" when the starter disengagement speed is reached. The starter disengagement speed is usually about 1200 rpm.

What is claimed is:

1. A method of determining motor oil quality, comprising the steps of:
   determining a viscosity of the motor oil during operation of an internal combustion engine;
   determining and evaluating a change of the viscosity of the motor oil determined in the viscosity determining step as a function of a temperature and frictional torque of the engine; and
   determining starter torque, the viscosity change determining and evaluating step including the substep of determining the frictional torque in accordance with the starter torque.

2. The method according to claim 1, wherein the starter torque is determined in the starter torque determining step in accordance with electric power consumed by the starter during start and a known starter characteristic curve.

3. The method according to claim 1, wherein the viscosity change determining and evaluating step includes the substep of determining the frictional torque in accordance with the starter torque and a consumed engine acceleration power.

4. A method of determining motor oil quality, comprising the steps of:
   determining a viscosity of the motor oil during operation of an internal combustion engine;
   determining and evaluating a change of the viscosity of the motor oil determined in the viscosity determining step as a function of a temperature and frictional torque of the engine; and
   determining whether the change of the viscosity is outside a range of −15% to +50% of a predefined viscosity value at a same temperature, the viscosity change determining and evaluating step being performed in accordance with the step of determining whether the change of the viscosity is outside the range of −15% to +50% of the predefined viscosity value at the same temperature.

5. A method of determining viscosity of motor oil of an internal combustion engine, comprising the steps of:
   determining an engine frictional torque; and
   determining the viscosity of the motor oil in accordance with the engine frictional torque;
   wherein the engine frictional torque is determined in the engine frictional torque determining step in accordance with engine data available in an engine controller; and
   wherein the engine data includes:
      an engine torque generated in accordance with at least one of an injection time and a throttle valve position;
      a signal that indicates whether a torque is transmitted to a drive train; and
      at least one signal relating to an operating condition of at least one auxiliary unit driven by the engine.

6. A method of determining viscosity of motor oil of an internal combustion engine, comprising the steps of:
   determining an engine frictional torque; and
   determining the viscosity of the motor oil in accordance with the engine frictional torque;
   wherein the engine frictional torque is determined in the engine frictional torque determining step in accordance with engine data available in an engine controller; and
   wherein the internal combustion engine is a diesel engine, the engine data including:
      a signal that indicates whether a torque is transmitted to a drive train;
      a load signal of a generator as a measure of an electric power generated by a generator;
      an engine rpm;
      an injected amount of fuel;
      an engine temperature; and
      an ambient temperature.

7. A method of determining viscosity of motor oil of an internal combustion engine, comprising the steps of:
   determining an engine frictional torque;
   determining the viscosity of the motor oil in accordance with the engine frictional torque; and
   determining a start torque and a consumed engine acceleration power, the engine frictional torque being determined in the engine frictional torque determining step in accordance with the start torque and the consumed engine acceleration power.

8. The method according to claim 7, wherein the start torque is determined in the start torque and consumed engine acceleration power determining step in accordance with an electric power consumed by a starter and a known starter characteristic.

9. The method according to claim 7, further comprising the step of measuring during start a time between start and a starter disengagement speed being reached, the engine frictional torque being determined in the engine frictional torque determining step in further accordance with the measure time and a known constant fuel amount injected during the measured time.

* * * * *